United States Patent
Loo (10) Patent No.: US 6,457,488 B2
(45) Date of Patent: Oct. 1, 2002

(54) STOPCOCK HAVING AXIAL PORT FOR SYRINGE TWIST ACTUATION

(76) Inventor: George Loo, 9814 Curwood Pl., Beverly Hills, CA (US) 90210

( * ) Notice: Subject to any disclaimer, the term of this patent is extended or adjusted under 35 U.S.C. 154(b) by 0 days.

(21) Appl. No.: 09/969,399

(22) Filed: Oct. 2, 2001

Related U.S. Application Data (63) Continuation-in-part of application No. 09/735,711, filed on Dec. 12, 2000, which is a continuation of application No. 09/004,437, filed on Jan. 8, 1998, now Pat. No. 6,158,467.

(51) Int. Cl.⁷ .............................................. F16K 11/08
(52) U.S. Cl. .................... 137/625.47; 222/387
(58) Field of Search ............................. 222/144.5, 326, 222/327, 386, 387; 137/625.47, 597

(56) References Cited

U.S. PATENT DOCUMENTS

| | | | |
|---|---|---|---|
| 1,854,307 A | | 4/1932 | Hapgood |
| 2,854,027 A | * | 9/1958 | Kaiser et al. .......... 137/625.47 |
| 2,907,349 A | | 10/1959 | White .................. 137/625.23 |
| 3,405,601 A | * | 10/1968 | Clarke ................... 137/625.47 |
| 4,275,823 A | * | 6/1981 | Credle, Jr. ................ 222/144.5 |
| 4,397,335 A | * | 8/1983 | Doblar et al. .......... 137/625.19 |
| 5,445,187 A | | 8/1995 | Farquhar ............... 137/625.32 |
| 5,927,560 A | * | 7/1999 | Lewis et al. ................ 222/263 |

\* cited by examiner

*Primary Examiner*—John Fox
(74) *Attorney, Agent, or Firm*—Stetina Brunda Garred & Brucker (57) ABSTRACT

A stopcock including a stopcock body including a central axial opening, and first and second stopcock luer connectors extending radially and in fluid communication with the central axial opening. The stopcock includes a stopcock core axially disposed within the central axial opening. The stopcock core includes an engagement end axially connectable with a syringe, an axial port formed at the engagement end for fluidly communicating with the syringe, a first radial port, and a first passage extending between the axial port and the first radial port. The stopcock core has a first position with the first radial port in fluid communication with the first stopcock luer connector. The stopcock core has a second position with the first radial port in fluid communication with the second stopcock luer connector. The core is rotatable from the first position to the second position upon the syringe being axially rotated.

10 Claims, 7 Drawing Sheets

STOPCOCK HAVING AXIAL PORT FOR SYRINGE TWIST ACTUATION

CROSS-REFERENCE TO RELATED APPLICATIONS

This is a continuation-in-part of application Ser. No. 09/735,711 filed on Dec. 12, 2000, which is a continuation of 09/004,437 U.S. Pat. No. 6,158,467, filed on Jan. 8, 1998, the contents of which are incorporated herein by reference.

STATEMENT RE: FEDERALLY SPONSORED RESEARCH/DEVELOPMENT (Not Applicable)

BACKGROUND OF THE INVENTION

The present invention relates generally to stopcocks, and more particularly to a stopcock having an axially rotatable core.

A stopcock is a cock or valve for stopping or regulating the flow of a fluid (including liquids and/or gasses). In medicine, a stopcock is most typically used for regulating the flow of intravenous ("IV") fluids or medications into, or out of, a patient as part of an intravenous system. In this regard, stopcocks provide a quick and sterile way for diverting intravenous fluid flow or medication into a patient by changing the flow path in the IV line system.

A stopcock can also be used to divert fluids or air into devices, such as for filling skin expanders with fluid or air during skin grafting, for filling breast implants with saline during breast augmentation procedures, for diverting spinal fluid into a manometer to measure spinal fluid pressure during a spinal tap, and for diluting viscous packed red blood cells with saline to make them less viscous for subsequent rapid infusion into the patient during transfusions.

Stopcocks are frequently used as a needle-less intravenous injection port. That is, once the initial IV injection port has been opened using a first needle, subsequent injections and infusions are possible through the same injection port via a stopcock having three ports separated by a shut off valve. Stopcocks provide an inexpensive method of avoiding needle-stick injuries and for a clinician to comply with the FDA mandate "to use needle-less injection techniques whenever possible". Typically, stopcocks are formed of injection molded plastic. As such, stopcocks are inexpensive and disposable after use on a single patient.

Early stopcock designs were simply used as "on and off" valves to start or stop intravenous infusions. Such designs contained two ports, an inlet port and an opposing outlet port. A lever extending from between the two ports was used as a shut off lever. Fluid was configured to only flow between the two ports. These first stopcocks designs were designated as two-port, one-way stopcocks.

Another prior art stopcock design includes a stopcock body with three ports which are arranged in a T-shaped configuration, and a stopcock core having a lever extending radially from an axial portion. The ports can be selected at the option of the user by rotating the lever to a position determined by the direction of desired flow. A "stop" tab is disposed on the stopcock body which prevents the lever of the stopcock from being turned to a position where all three ports are open and flow into one another at one time, i.e., such that the T-shaped path of the body and the T-shaped path of the core are fully aligned. Because fluid can flow three different ways, these stopcocks are designated as three-port, three-way stopcocks.

Figure 1A:
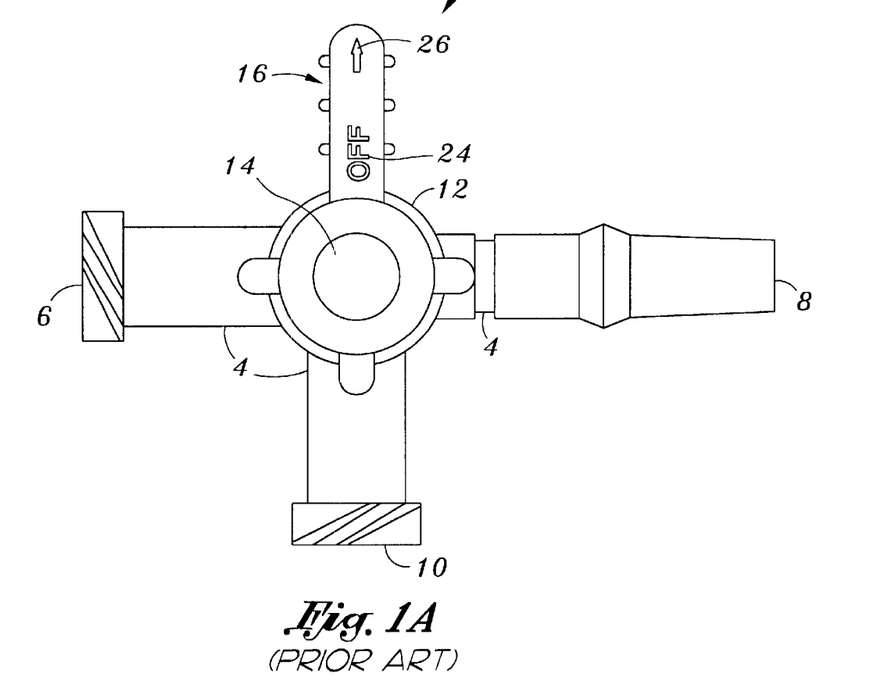
FIG. 1A is a top view of a prior art three-port, four-way stopcock.

Referring now to FIG. 1A, there is depicted a prior art stopcock 2 which is a three-port, four-way stopcock. It does not have a stop tab as in the threeport, three-way stopcock to prevent the lever from being turned to a position opposite the right angled port. The stopcock 2 includes a body 4 having an entry port 6, an exit port 8 and an injection port 10, and a core 12. The core 12 includes a rotating axial portion 14 connected to a lever 16.

Figure 1B:
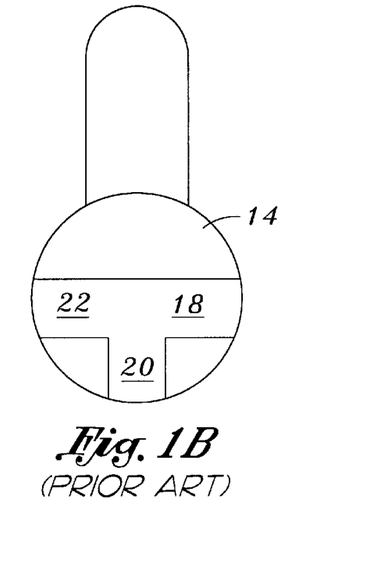
FIG. 1B is a cross-sectional/top view of a core of the prior art three-port, four-way stopcock of FIG. 1A.
Figure 1C:
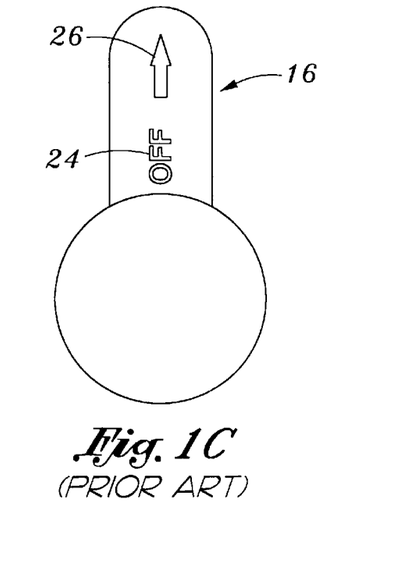
FIG. 1C is a top view of a core of the prior art three-port, four-way stopcock of FIG. 1A.

Referring to FIG. 1B and FIG. 1C, the axial portion 14 of the core 12 has a first flow channel 18, a second flow channel 20 and a third flow channel 22 which form a confluent "T" configuration. The lever 16 generally includes the word "off" 24 and an arrow 26 molded on its upper surface to show which direction fluid will not flow. The arrow 26 and the word "off" 24 do not directly indicate to the user which way the medication or fluid will flow.

The stopcock 2 is a four-way stopcock because fluid can flow in four different ways. First, when the lever 16 points toward the entry port 6, fluid can flow between the injection port 10 and exit port 8. Second, when the lever 16 points toward the injection port 10, fluid can flow between the entry port 6 and exit port 8. Third, when the lever 16 points toward the exit port 8, fluid can flow between the entry port 6 and injection port 10. Finally, when the lever 16 points opposite the injection port 10, i.e., toward no port, fluid can flow between all three ports 6, 8, 10 at one time.

Figure 2:
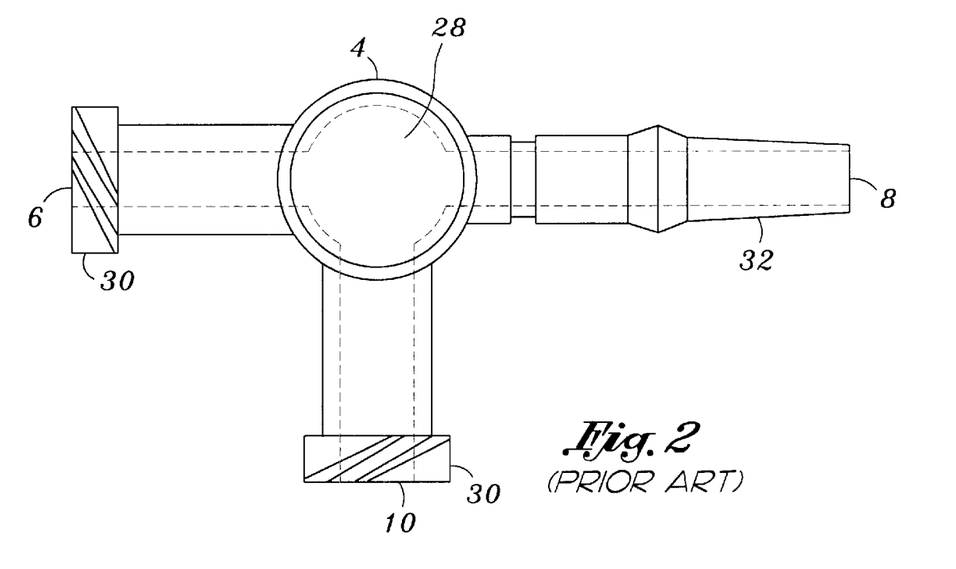
FIG. 2 is a top view of a body of the prior art three-port, four-way stopcock of FIG. 1.

Referring to FIG. 2, there is depicted the body 4 of stopcock 2. The entry port 6, exit port 8 and injection port 10 are located in a single horizontal plane and are confluent at a central chamber 28, which is filled with the axial portion 14 of the core 12 when the stopcock 2 is assembled. The entry port 6 has a female luer lock connector 30 and is the main fluid entry end of the stopcock 2. It usually is connected to a male luer-lock connector 32 from an IV set connected to a bag of an IV fluid. The exit port 8 has a male luer lock or luer slip connector 32 and is the fluid exit end of the stopcock 2 and is usually connected to a female luer lock connector 30 of an IV extension set which ultimately connects to an IV catheter in a patient. The injection port 10 protruding perpendicularly from the middle of the straight line flow path formed by the entry port 6 and exit port 8 has a female luer lock connector 30 and is used for adding medication or fluids to the IV system.

Figure 3:
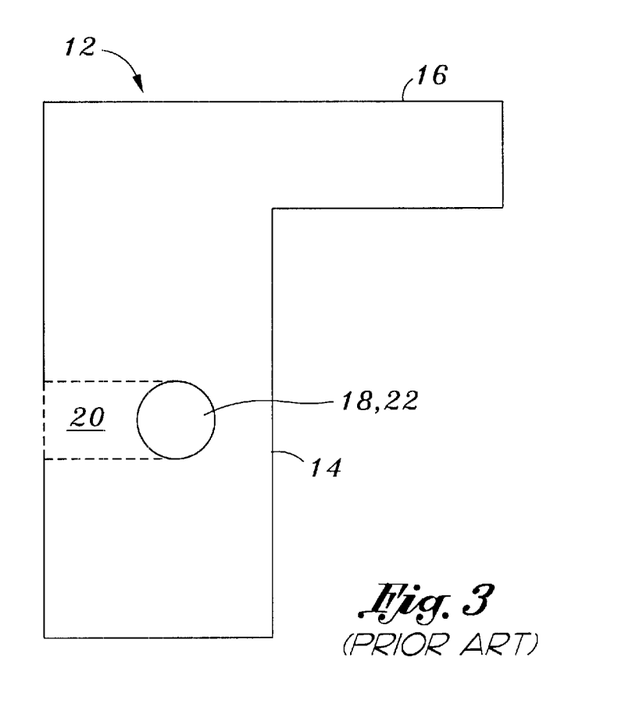
FIG. 3 is a side view of the core of the prior art three-port, four-way stopcock of FIG. 1.
Figures 4, 5:
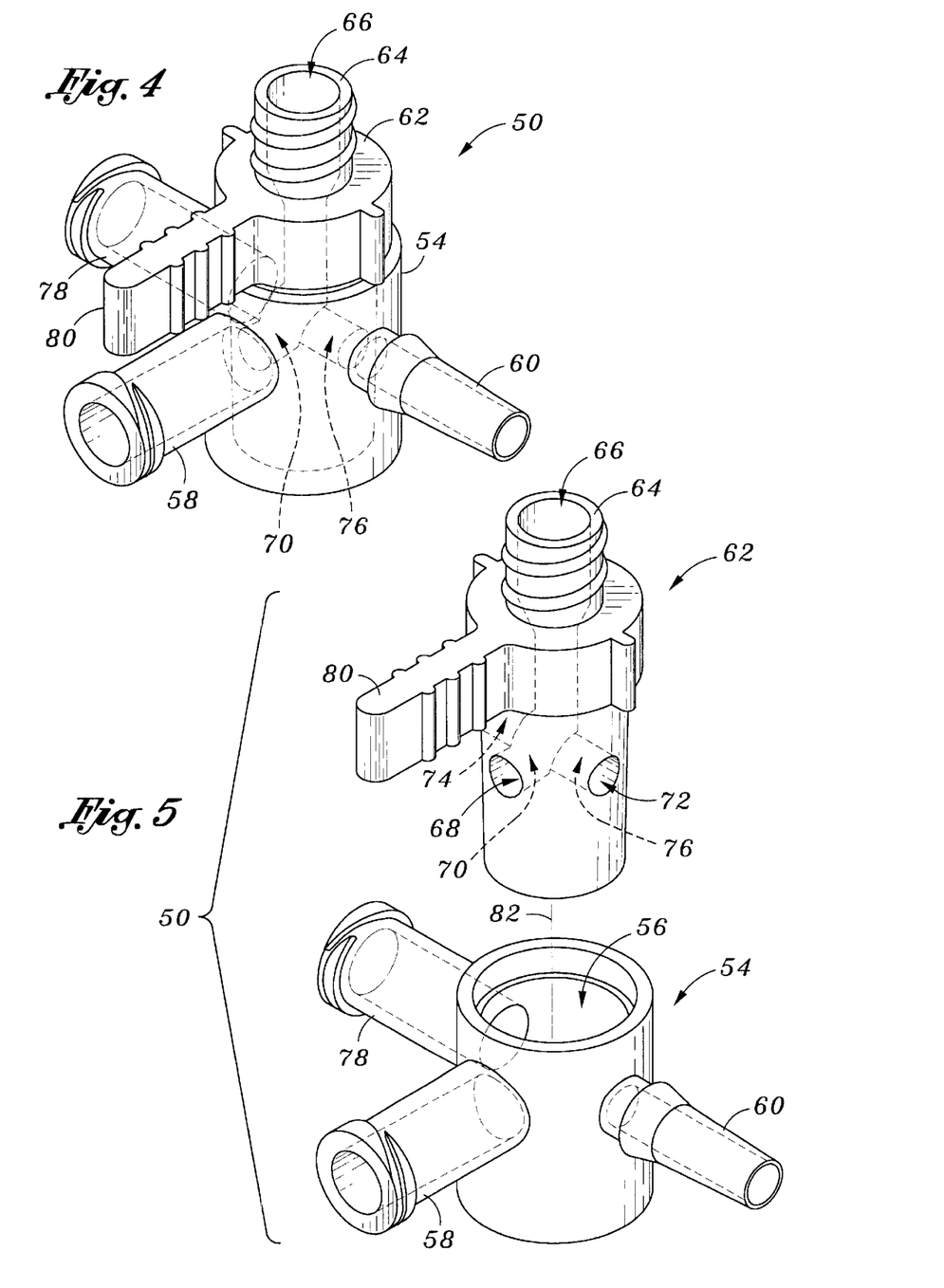
FIG. 4 is a perspective view of a stopcock constructed according to an aspect of the present invention.
FIG. 5 is an exploded view of the stopcock of FIG. 4 depicting a stopcock core and stopcock body.
Figures 6, 7, 8:
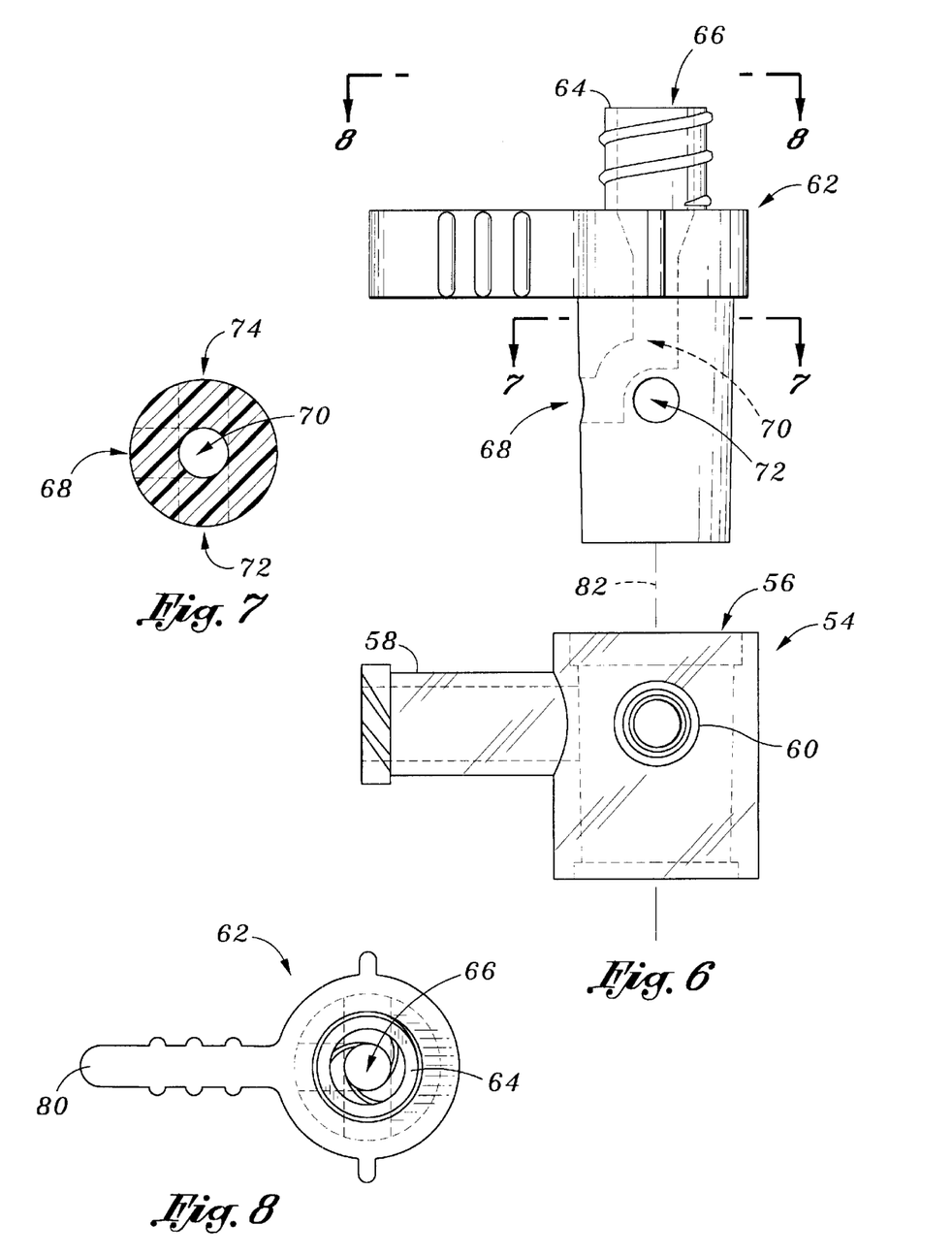
FIG. 6 is a side view of the stopcock of FIG. 5 with internal passages shown in phantom.
FIG. 7 is a cross-sectional top view of the stopcock core as seen along axis 7—7 of FIG. 6.
FIG. 8 is a top view of the stopcock core as seen along axis 8—8 of FIG. 6.

Referring to FIG. 3, there is depicted a core 12 having the axial portion 14 and the lever 16. The lever 16 rotates in a horizontal plane which is parallel to the horizontal plane formed by the three fluid flow ports 6, 8 and 10. The procedure a clinician must follow to perform a typical IV injection or infusion using a conventional three-port, four-way stopcock 2 is fraught with difficulty and risk. An examination of this procedure makes clear the need for an improvement, such as that of the present invention described further below.

A typical intravenous setup using a three-port, four-way stopcock 2 has the exit port 8 typically connected to an IV extension tubing which is subsequently connected to an IV catheter in the patients vein. The entry port 6 is connected to a main IV administration set which is in turn connected to a bag of IV fluid, and the injection port 10 normally has a syringe or a secondary IV fluid line connected to it. When a syringe is attached to the injection port 10, the bulk and length of the syringe requires that the syringe-stopcock assembly sits on a surface wherein a single plane is formed by the flow ports 6, 8, 10 of the stopcock 2 and the attached syringe. The axial portion 14 then extends vertically upward from, and the lever 16 rotates in a plane parallel to, that surface. To turn the lever 16 in a desired direction, a first hand of a clinician is held palm up in a horizontal plane, with the fingers pointing upward in a vertical direction, to stabilize the syringe-stopcock assembly, and a second hand of the clinician is held above the lever 16, with fingers pointing in a downward, vertical direction, for grasping and rotating the lever 16.

This prior art stopcock arrangement is awkward for the clinician. With the first hand below and the second hand above the stopcock 2, the clinician must first determine which way to turn the lever 16 to obtain the desired fluid flow, and then he or she must turn it in the correct direction, either clockwise or counter-clockwise, with fingers of the second hand. When the clinician is assured that the stopcock 2 is secure in the grasp of the first hand only, the second hand releases the lever 16 and grasps the barrel of the syringe attached to the injection port 10. The second hand then pushes or pulls the plunger of the syringe to give an injection of medication or to aspirate fluid. The second hand must next move from the syringe barrel back to its previous position grasping the lever 16 of the stopcock 2 and rotating it back to its original position. This procedure is cumbersome and time consuming, and involves twice moving one hand between two perpendicular planes.

It is therefore evident that there exists a need in the art for an improved stopcock in comparison to the prior art designs.

BRIEF SUMMARY OF THE INVENTION

In accordance with an aspect of the present invention, there is provided a stopcock for use with a syringe. The stopcock includes a stopcock body. The stopcock body includes a central axial opening formed in the stopcock body. The stopcock body further includes a first stopcock luer connector extending radially from the stopcock body and in fluid communication with the central axial opening. The stopcock body further includes a second stopcock luer connector extending radially from the stopcock body and in fluid communication with the central axial opening. The stopcock further includes a stopcock core axially disposed within the central axial opening. The stopcock core includes an engagement end axially connectable with the syringe. The stopcock core further includes an axial port formed at the engagement end for fluidly communicating with the syringe. The stopcock core further includes a first radial port formed in the stopcock core. The stopcock core further includes a first passage formed in the stopcock core extending between the axial port and the first radial port. The stopcock core has a first position with the first radial port in fluid communication with the first stopcock luer connector. The stopcock core has a second position with the first radial port in fluid communication with the second stopcock luer connector. The stopcock core is rotatable from the first position to the second position upon the syringe being axially connected to the engagement end and axially rotated.

Advantageously, the stopcock core may be rotated about a longitudinal axis as initiated by rotation of an attached syringe. Thus, rotation of the syringe is contemplated to selectively direct the direction of the first radial port in relation to the stopcock body, such as between the first and second positions.

According to an embodiment of the present invention, the stopcock core has a second radial port and a third radial port formed in the stopcock core, and a second passage formed in the stopcock core extending between the second radial port and the third radial port. The third radial port is disposed opposite the second radial port. The first radial port is disposed perpendicular to the second and third radial ports. The second radial port is in fluid communication with the second stopcock luer connector with the stopcock core in the first position. In addition, the stopcock body may have a third stopcock luer connector extending radially from the stopcock body and in fluid communication with the central axial opening. The third radial port is in fluid communication with the third stopcock luer connector with the stopcock core in the first position. Further, the engagement end may be a female connector, and the syringe may have a male connector for engaging the engagement end in fluid communication. The engagement end may be threadedly connectable with the syringe. The first stopcock luer connector may be a male connector, and the second stopcock luer connector may be a female connector.

Accordingly, the present invention represents a significant advance in the art.

BRIEF DESCRIPTION OF THE DRAWINGS

These, as well as other features of the present invention, will become more apparent upon reference to the drawings wherein.

DETAILED DESCRIPTION OF THE INVENTION

Referring now to the drawings wherein the showings are for purposes of illustrating a preferred embodiment of the present invention only, and not for purposes of limiting the same, FIGS. 4–11 illustrate a stopcock according to aspects of the present invention.

In accordance with an aspect of the present invention, there is provided a stopcock 50 for use with a syringe 52. The stopcock 50 includes a stopcock body 54. The stopcock body 54 includes a central axial opening 56 formed in the stopcock body 54. The stopcock body 54 further includes a first stopcock luer connector 58 extending radially from the stopcock body 54 and in fluid communication with the central axial opening 56. The stopcock body 54 further includes a second stopcock luer connector 60 extending radially from the stopcock body 54 and in fluid communication with the central axial opening 56. The stopcock 50 further includes a stopcock core 62 axially disposed within the central axial opening 56. The stopcock core 62 includes an engagement end 64 axially connectable with the syringe 52. The stopcock core 62 further includes an axial port 66 formed at the engagement end 64 for fluidly communicating with the syringe 52. The stopcock core 62 further includes a first radial port 68 formed in the stopcock core 62. The stopcock core 62 further includes a first passage 70 formed in the stopcock core 62 extending between the axial port 66 and the first radial port 68. The stopcock core 62 has a first position with the first radial port 68 in fluid communication with the first stopcock luer connector 58. The stopcock core 62 is shown in the first position in FIGS. 4, 9 and 10. The stopcock core 62 has a second position with the first radial port 68 in fluid communication with the second stopcock luer connector 60. The stopcock core 62 is shown in this second position in FIG. 11. The stopcock core 62 is rotatable from the first position to the second position upon the syringe 52 upon being axially connected to the engagement end 64 and axially rotated.

Advantageously, the stopcock core 62 may be rotated about a longitudinal axis 82 as initiated by rotation of an attached syringe 52. Thus, rotation of the syringe 52 is contemplated to selectively direct the direction of the first radial port 68 in relation to the stopcock body 54, such as between the first and second positions.

The syringe 52 is typically provided with a luer tip 94 which is of a male connector configuration. In this regard, the engagement end 64 stopcock core 62 is preferably a female connector for engaging the luer tip 94 in fluid communication. It is contemplated that press-fit engagement of the luer tip 94 with the engagement end 64 is sufficient to allow the rotation of the syringe 52 to initiate rotation of the stopcock core 62. Further, the engagement end 64 may be threadedly connectable with the syringe 52 at the luer tip 94. This further provides a secure engagement between the syringe 52 and stopcock core 62 during rotation. This is especially the case where the syringe 52 is rotated in a manner which furthers the threaded engagement with the engagement end 64. However, it is contemplated that the syringe 52 may be rotated in either clockwise or counter-clockwise directions.

According to an embodiment of the present invention, the stopcock core 62 has a second radial port 72 and a third radial port 74 formed in the stopcock core 62. The third radial port 74 is disposed opposite the second radial port 72. A second passage 76 is formed in the stopcock core 62 extending between the second radial port 72 and the third radial port 74. Preferably, the first radial port 68 is disposed perpendicular to the second and third radial ports 72, 74. The first, second and third radial ports 68, 72, 74 extend radially from the longitudinal axis 82 in generally a common plane.

With the stopcock core 62 in the first position, the second radial port 72 is in fluid communication with the second stopcock luer connector 60. In addition, the stopcock body 54 may have a third stopcock luer connector 78 extending radially from the stopcock body 54 and in fluid communication with the central axial opening 56. With the stopcock core 62 in the first position, the third radial port 74 is in fluid communication with the third stopcock luer connector 78. In the configuration shown, the first stopcock luer connector 58 is a male connector, and the second stopcock luer connector 60 is a female connector.

The first, second or third stopcock luer connectors 58, 60, 78 preferably extend radially from the stopcock body 54 in generally a common plane. As such, the stopcock core 62 may be selectively rotated such that the first radial port 68 may fluidly communicate with the any one of the first, second or third stopcock luer connectors 58, 60, 78. Further, the stopcock body 54 may include additional stopcock luer connectors (not shown) similar to first, second or third stopcock luer connectors 58, 60, 78. For example, an additional stopcock luer connector may be provided opposite the first stopcock luer connector 58. In this regard, the stopcock core 62 may be selectively rotated such that the first radial port 68 may fluidly communicate with the any one of a number of stopcock luer connectors in addition to the first, second or third stopcock luer connectors 58, 60, 78 shown.

Suitable specifications of the stopcock luer connectors 58, 60, 78 of the stopcock body 54 and the engagement end 64 of the stopcock core 62 are specified by the American National Standards Institute, Inc. (ANSI) under the American National Standard for Medical Material-Luer Taper Fittings—Performance, and by the International Organization for Standardization under ISO 594/1, Conical fittings with a 6% (Luer) taper for syringes, needles and certain other medical equipment—Part 1: General Requirements. In general, such male connectors have a cylindrical dimension with a 6% taper, having a 0.155 inch diameter at one end, a 0.170 inch diameter at the other end, and extends over a distance of 0.250 inches.

The stopcock core 62 is preferably formed of a unitary piece of injection molded plastic. Similarly, the stopcock body 54 is preferably formed of a unitary piece of injection molded plastic. The stopcock core 62 is press-fit assembled within the central opening 56 of the stopcock body 54. The stopcock core 62 and the stopcock body 54 are cooperatively configured for sealed engagement while assembled, and may include snap-fit surface details not shown.

The stopcock core 62 may further include a lever 80 which extends radially. The lever 80 is preferably aligned with the first radial port 68. In this regard, the lever 80 may serve to indicate the location of the first radial port 68 which is not readily observed when assembled within the stopcock body 54. Further, the lever 80 may be utilized as leverage for rotating the stopcock core 62.

The stopcock 50 of the embodiment shown is configured to facilitate fluid flow in four different ways. In this regard, with the stopcock core 62 in the first position, fluid may flow between the axial port 66 and the first luer connector 58, through the first passage 70 and the first radial port 68. With the stopcock core 62 rotated from the first position, fluid may also flow between the axial port 66 and the second or third luer connector 60, 78, through the first passage 70 and the first radial port 68. In addition, with the stopcock core 62 in the first position, a separate fluid may flow between, the second and third luer connector 60, 78, through the second passage 76 and the second and third radial ports 72, 74. As such, in the embodiment shown, the stopcock 50 is a four-way, four-port configuration.

Figure 9:
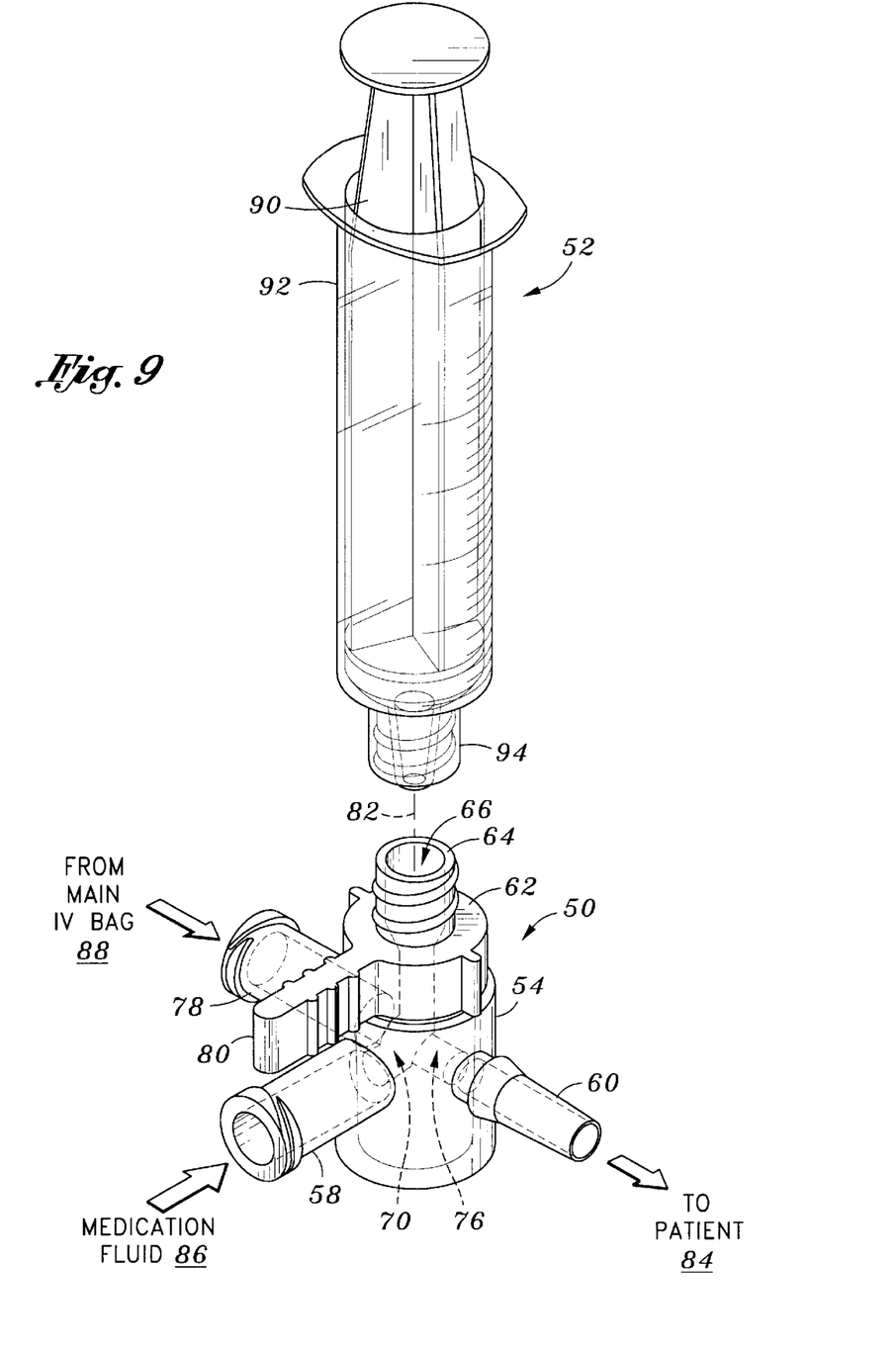
FIG. 9 is a perspective view of the stopcock of the present invention as shown with a syringe.

In practice, the configuration shown of the stopcock 50 has particular application for medication fluid delivery to a patient 84 connected to a main IV bag 88. Referring now to FIG. 9, the first stopcock luer connector 60 may be connected to the patient 84 (such a via a female luer lock connector of an IV extension set connected to an IV catheter in the patient 82, not shown). The second stopcock luer connector 78 may be connected to the main IV bag 88. Fluid flow from the main IV bag 88 may flow through the second stopcock connector 78, the third radial port 74, the second passage 76, the second radial port 72, and the second stopcock luer connector 60.

Figure 10:
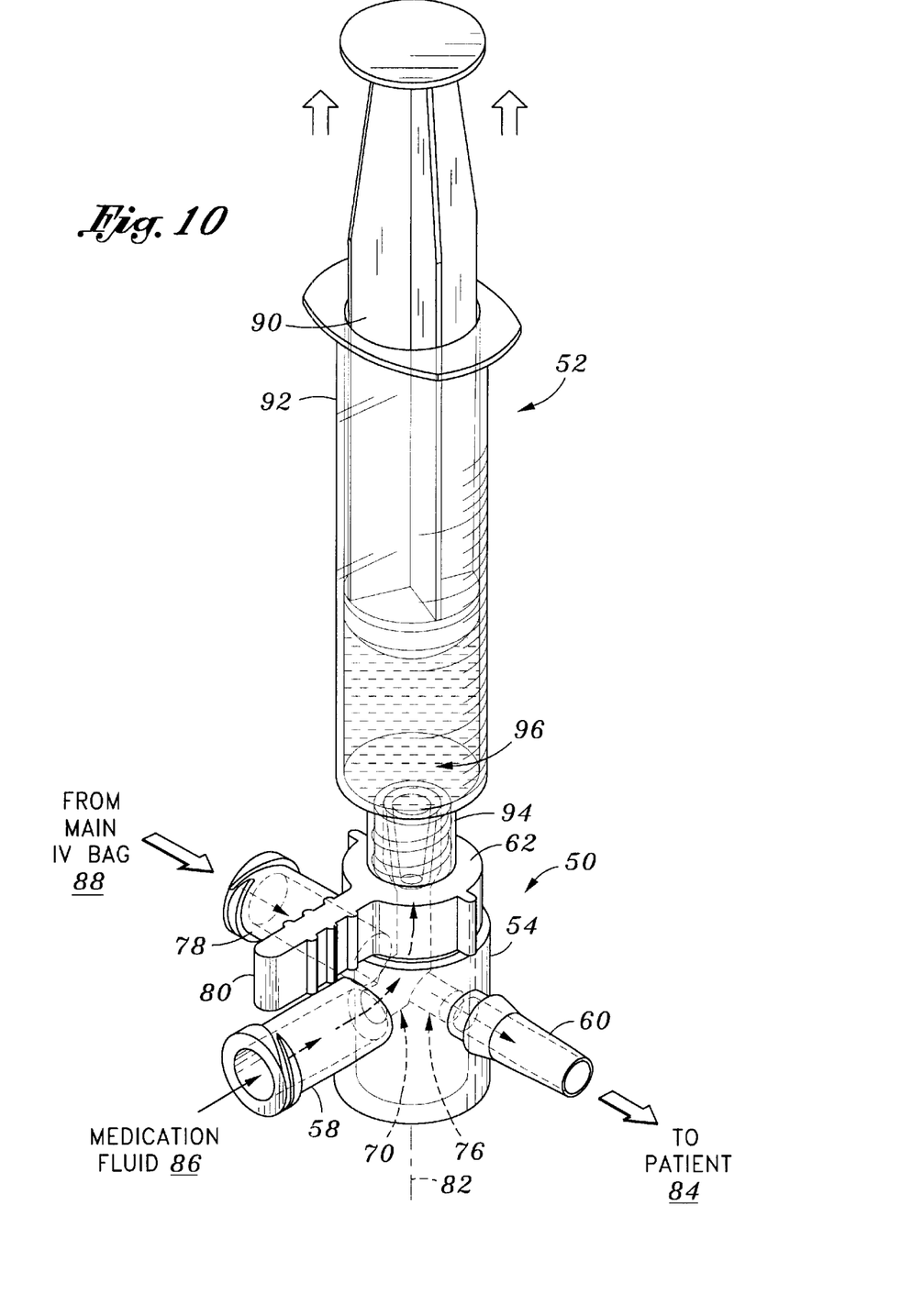
FIG. 10 is a perspective view of the stopcock of the present invention as shown with an engaged syringe receiving fluid through the stopcock.

Should a clinician be required to deliver medication fluid 86 to the patient 84, the clinician may connect the medication fluid 86 to the first luer connector 58 of the stopcock body 54. The clinician may further connect the syringe 52 to the engagement end 64 of the stopcock core 62. As depicted in FIG. 10, the clinician may then withdraw a plunger 90 away from a barrel 92 of the syringe 52 to create a vacuum force for drawing syringe fluid 96 into the barrel 92 of the syringe 52 from the medication fluid 86. It is contemplated that this may be done with a single hand of the clinician. A flow path is established from the medication fluid 86, through the first stopcock luer connector 58, the first radial port 68, the first passage 70, the axial port 66 and the luer tip 94. Advantageously, this process does not require interruption of delivery of fluid from the main IV bag 88 to the patient 84. This is because the stopcock 50 allows for the simultaneous flow paths through the first and second passages 70, 76 while the stopcock core 62 is in the first position.

Once the desired amount of syringe fluid 96 is obtained within the syringe 52, the clinician may rotate the syringe 52 to initiate rotation of the engaged stopcock core 62 from the first position to the second position. This may conveniently be accomplished with a twisting motion of the clinician's wrist. Further, this may be accomplished with the very same hand that the clinician utilizes for withdrawing the plunger 90 to obtain the syringe fluid 96.

Figure 11:
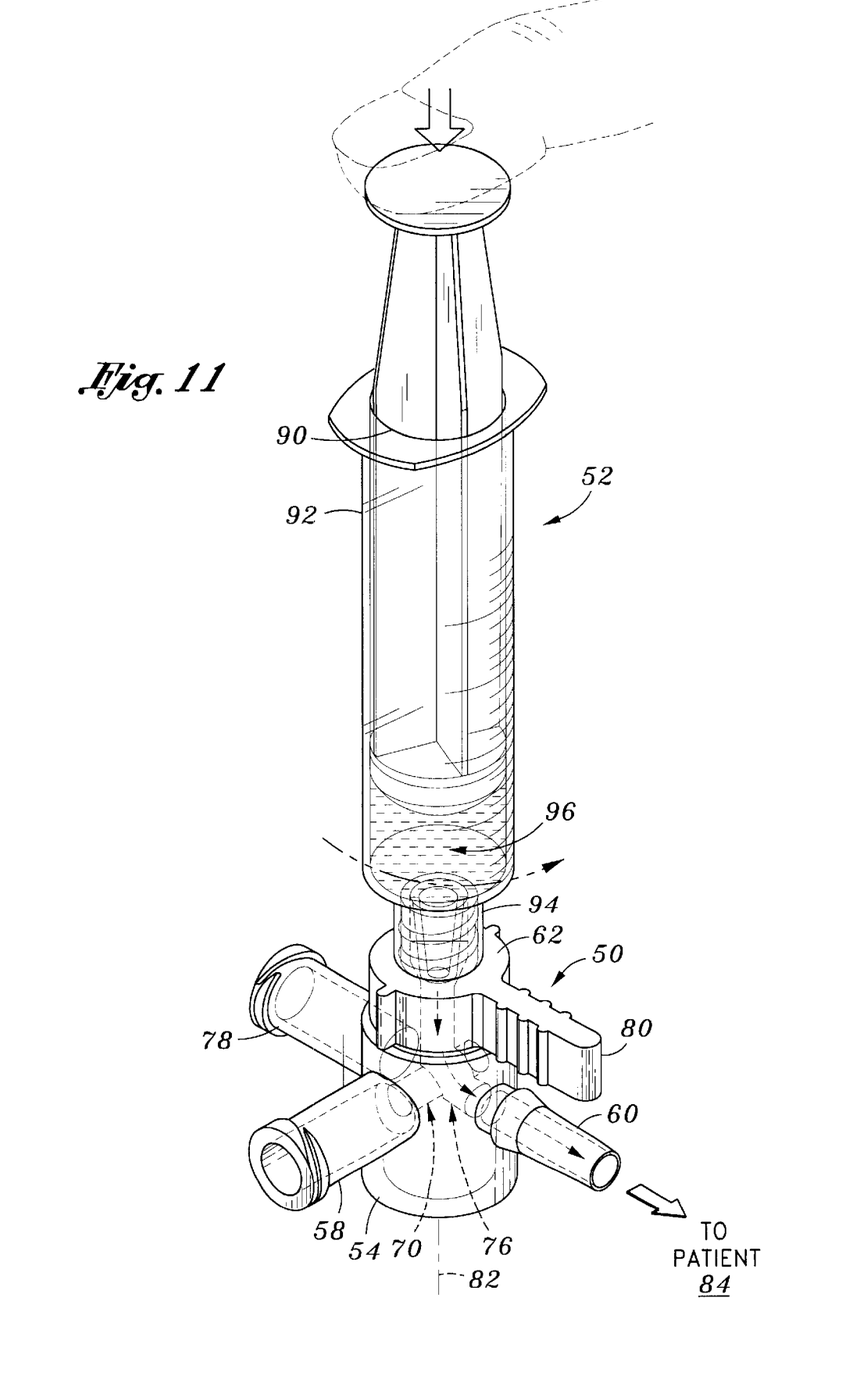
FIG. 11 is a perspective view of the stopcock of the present invention as shown with an engaged syringe which is axially rotated in comparison to FIG. 10 and is shown injecting fluid through the stopcock.

Having rotated the stopcock core 62 into the second position, a fluid path may be established from the syringe 52 to the patient 84 as shown in FIG. 11. As such, the clinician may depress the plunger 90 into the barrel 92 of the syringe 52 thereby injecting the syringe fluid 96 through the luer tip 94 into the stopcock 50. The flow path continues through the axial port 66, the first passage 70, the first radial port 68, and the second stopcock luer connector 60 to the patient 84.

Advantageously, should additional injections be required the clinician may simply twist the syringe 52 from the second position to the first position to refill and re-inject the patient 84 by repeating the procedure. To the extent that no additional injection is immediately required, the clinician may simply twist the syringe 52 to rotate the stopcock core 62 back to the first position in order to allow the flow path from the main IV bag 88 to the patient 84 through the stopcock 50 (or the syringe 52 may be rotated 180 degrees from the first position.

Additional modifications and improvements of the present invention may also be apparent to those of ordinary skill in the art. Thus, the particular combination of parts described and illustrated herein is intended to represent only one embodiment of the present invention, and is not intended to serve as limitations of alternative devices within the spirit and scope of the invention.

What is claimed is:

1. A stopcock for use with a syringe, the stopcock comprising:
    a stopcock body including:
        a central axial opening formed in the stopcock body;
        a first stopcock luer connector extending radially from the stopcock body and in fluid communication with the central axial opening; and
        a second stopcock luer connector extending radially from the stopcock body and in fluid communication with the central axial opening; and
    a stopcock core axially disposed within the central axial opening, the stopcock core including:
        an engagement end axially connectable with the syringe;
        an axial port formed at the engagement end for fluidly communicating with the syringe;
        a first radial port formed in the stopcock core; and
        a first passage formed in the stopcock core extending between the axial port and the first radial port; and
    wherein the stopcock core has a first position with the first radial port in fluid communication with the first stopcock luer connector; and
    wherein the stopcock core has a second position with the first radial port in fluid communication with the second stopcock luer connector, the stopcock core is rotatable from the first position to the second position upon the syringe upon being axially connected to the engagement end and axially rotated.

2. The stopcock of claim 1 wherein the stopcock core has a second radial port and a third radial port formed in the stopcock core, and a second passage formed in the stopcock core extending between the second radial port and the third radial port.

3. The stopcock of claim 2 wherein the third radial port is disposed opposite the second radial port.

4. The stopcock of claim 2 wherein the first radial port is disposed perpendicular to the second and third radial ports.

5. The stopcock of claim 2 wherein the second radial port is in fluid communication with the second stopcock luer connector with the stopcock core in the first position.

6. The stopcock of claim 2 wherein the stopcock body has a third stopcock luer connector extending radially from the stopcock body and in fluid communication with the central axial opening, the third radial port is in fluid communication with the third stopcock luer connector with the stopcock core in the first position.

7. The stopcock of claim 1 wherein the engagement end is a female connector, and the syringe has a male connector for engaging the engagement end in fluid communication.

8. The stopcock of claim 1 wherein the engagement end is threadedly connectable with the syringe.

9. The stopcock of claim 1 wherein the first stopcock luer connector is a male connector.

10. The stopcock of claim 1 wherein the second stopcock luer connector is a female connector.

* * * * *